(12) United States Patent
Hammonds et al.

(10) Patent No.: US 8,506,777 B2
(45) Date of Patent: Aug. 13, 2013

(54) LOCALIZED CORROSION MONITORING DEVICE FOR LIMITED CONDUCTIVITY FLUIDS

(75) Inventors: Paul Hammonds, Dubai (AE); Vladimir Jovancicevic, Richmond, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 13/364,760

(22) Filed: Feb. 2, 2012

(65) Prior Publication Data

US 2012/0132526 A1 May 31, 2012

Related U.S. Application Data

(62) Division of application No. 12/356,695, filed on Jan. 21, 2009, now Pat. No. 8,133,383.

(60) Provisional application No. 61/022,944, filed on Jan. 23, 2008.

(51) Int. Cl.
*G01N 27/26* (2006.01)

(52) U.S. Cl.
USPC .......................... 204/404; 205/775.5; 324/700

(58) Field of Classification Search
USPC ............... 324/700; 204/404; 205/775.5
See application file for complete search history.

(56) References Cited

U.S. PATENT DOCUMENTS

| | | | |
|---|---|---|---|
| 3,609,549 A * | 9/1971 | Hausler et al. | 324/700 |
| 4,181,882 A * | 1/1980 | Isaacs et al. | 205/775.5 |
| 5,139,627 A * | 8/1992 | Eden et al. | 205/775.5 |
| 5,243,297 A | 9/1993 | Perkins et al. | |
| 5,627,749 A | 5/1997 | Waterman et al. | |
| 6,132,593 A | 10/2000 | Tan | |
| 6,280,603 B1 | 8/2001 | Jovancicevic | |
| 6,919,729 B2 | 7/2005 | Tiefnig | |
| 8,133,383 B2 | 3/2012 | Hammonds et al. | |
| 2005/0211570 A1 | 9/2005 | Jovancicevic et al. | |
| 2006/0144719 A1 | 7/2006 | Gill et al. | |
| 2007/0017822 A1 | 1/2007 | Gill et al. | |
| 2007/0256942 A1 * | 11/2007 | Atherton | 205/775.5 |

OTHER PUBLICATIONS

ASTM G 96-90 "Standard Guide for On-Line Monitoring of Corrosion in Plant Equipment" (Electrical and Electrochemical Methods), Oct. 1996.
J. J. Moloney, et al., "In Situ Assessment of Pitting Corrosion and Its Inhibition Using a Localized Corrosion Monitoring Technique," Corrosion Science Section, Jun. 2010, pp. 065003-1-065003-18, vol. 66, No. 6.

* cited by examiner

*Primary Examiner* — Luan Van
*Assistant Examiner* — Maris R Kessel
(74) *Attorney, Agent, or Firm* — Mossman Kumar & Tyler PC

(57) ABSTRACT

A localized corrosion monitoring (LCM) device is modified to obtain polarization resistance ($R_p$) from electrical resistance of a probe having a strip of metal under investigation (test electrode), a reference electrode and a temperature sensor (e.g. thermocouple). This configuration allows the probe to be used in areas where only a thin film of conductive fluid is available or required to provide potential monitoring. Thus, the applicability of the LCM technique is broadened. All the above devices are expected to be configured in one item of equipment, except for the probe which may be remotely located from the rest of the equipment.

13 Claims, 1 Drawing Sheet

LOCALIZED CORROSION MONITORING DEVICE FOR LIMITED CONDUCTIVITY FLUIDS

CROSS-REFERENCE TO RELATED APPLICATIONS

This application is a divisional application from U.S. Ser. No. 12/356,695 filed Jan. 21, 2009, issued as U.S. Pat. No. 8,133,383 B2 on Mar. 13, 2012, which in turn claims the benefit of U.S. Provisional Patent Application No. 61/022,944 filed Jan. 23, 2008.

TECHNICAL FIELD

The present invention relates to electrochemical methods and systems for measuring corrosion rate, particularly to methods and apparatus for evaluating localized corrosion, and most particularly relates in a non-limiting embodiment, to methods and apparatus for measuring localized corrosion in hydrocarbon pipelines, transportation systems, processing vessels and fluid handling equipment by obtaining polarization resistance ($R_p$).

DESCRIPTION OF THE RELATED ART

Localized corrosion of equipment is a serious problem in many industries and processes. In particular, corrosion failures in many oil and gas production systems, oil/gas/water transmission pipelines, petrochemical and chemical processing plants, fossil fuel and nuclear power plants involve localized corrosion. Localized corrosion may result in loss of production, increase in maintenance costs, environmental pollution and potential health and safety hazards, etc. It is important that the occurrence of localized corrosion is identified and the severity determined in advance of structural failure, particularly catastrophic failure. In addition, the ability of chemical additives to inhibit localized corrosion and prevent such failures needs to be determined.

Localized corrosion is the selective removal of metal by corrosion at small areas or zones on a metal surface in contact with a corrosive environment, usually a liquid. While pitting is a type of localized corrosion, the locally corrosive pits may eventually cover substantial portions of a corroded electrically conductive article's surface. Localized corrosion may occur when small local sites are attacked at a much higher rate than the rest of the surface. Alternatively, a film or surface may protect the majority of the structure, where a relatively small area is under localized corrosion attack. Localized corrosion occurs when corrosion works with other destructive forces such as stress, fatigue, erosion and chemical attacks. Localized corrosion may cause more damage than any of these destructive forces individually.

The problems resulting from localized corrosion have been dealt with for many years with variable success. Localized corrosion is highly stochastic in nature and its occurrence is fairly unpredictable. Thus, it is important that statistical analysis is carried out when studying or monitoring localized corrosion. Currently, localized corrosion is studied or monitored by measuring directly large features (e.g. pits) on the surface by using standard optical microscopy with limited spatial resolution. Indirect methods are also used, such as electrochemical noise, to provide indication of the probability of localized (e.g. localization index) corrosion.

Electrochemical noise (ECN) may be defined as the spontaneous fluctuations of current and potential generated by corrosion reactions. Various methods have been used to determine corrosion rates, including a linear polarization resistance (LPR) method. In LPR a direct current (DC) signal is applied to a corroding cell consisting of two or three electrodes and the resulting DC polarization is monitored. Provided that the applied current is small and that the potential shift is less than 20 millivolts (mV), the response is linear in most cases and the measured resistance, commonly known as the polarization resistance ($R_p$), may be related inversely to the rate of the uniform corrosion attack. Other techniques include the application of electrochemical impedance spectroscopy (EIS) in which a sine wave current or potential is applied. In a similar manner to the linear polarization technique, and the sine wave potential or current resulting from the applied current or potential is monitored. Alternatively, a pseudo random noise signal can be applied to a corroding cell, with the electrochemical impedance obtained by time or frequency domain transformations.

Although the above techniques are widely employed, they (1) possess limitations in that they only provide information on uniform (general) corrosion conditions because they provide an average signal for the surface of the electrode being monitored; and (2) depending upon the environment, metallic material, and corrosion type, the assumption that the corrosion rate is inversely proportional to the measured charge transfer or polarization resistance is invalid because the corrosion is of a localized nature. These problems have been addressed by monitoring localized corrosion via the utilization of electrochemical potential noise analysis. Alternatively, by coupling current analysis with electrochemical potential noise analysis further information can be obtained. For example, two similar electrodes can be coupled together via a zero resistance ammeter with the output of the zero resistance ammeter passed to the input of the electrochemical noise analysis system. In this way, the fluctuation of the coupling current may be analyzed in essentially a similar manner as for the electrochemical potential noise analysis described previously.

Systems which employ two working electrodes fabricated with the same material and exposed to the same corrosion conditions as the metallic surface to be tested are known. Such systems further employ a device for measuring the coupling current between the working electrodes, a device for measuring electrochemical potential noise originating from the electrodes, and a device for comparing the coupling current with the electrochemical current noise to provide an output indicative of the degree to which corrosion is localized. The systems utilize open circuit potential conditions, employing two working electrodes in an electrolyte environment wherein both electrodes are short circuited with a low resistance amp meter. The current between these two working electrodes is the result of corrosion occurring on them, with the measurement of the net current relating to the corrosion on both of them. Disadvantages of this system, however, include the fact that the working electrodes need to be identical to obtain accurate readings and obtaining such identical electrodes is difficult, if not impossible. Another problem is that it is unknown which electrode is responding to reveal the corrosion, due to the fact that this system requires the use of two working electrodes which limits where such systems can be employed. Furthermore, distinguishing between various types of localized corrosion is, at minimal, difficult due to the fact that both electrodes contribute to the system response.

What is needed in the art is a simplified corrosion rate detection system and method. The methods and apparatus described herein overcome some disadvantages of the prior methods and apparatus by providing corrosion detection calculation capability for localized metal corrosion.

SUMMARY

In one non-limiting embodiment there is provided a method for measuring localized corrosion that includes placing a test electrode (metal strip) of a metal under investigation having length L in contact with a conductive fluid. A reference electrode is placed in proximity to test electrode. The method further involves placing a temperature sensor in proximity to the metal strip. The resistance across the length L of the test electrode is measured over a time period $\Delta t$ to give first and second resistance values $R_1$ and $R_2$. Changes in conductance of the test electrode (metal strip) due to temperature are calculated from the specific conductance of the metal electrode and the measured temperature. This conductance due to temperature fluctuation is converted to a resistance and subtracted from measurements of $R_1$ and $R_2$ in order to obtain the desired temperature-independent value of electrical resistance. It should be noted that there is the electrical resistance of the metal strip and the polarization resistance of the metal strip. The latter is polarization with respect to a reference electrode and the circuit includes the intervening fluid; whereas the electrical resistance is that which one would measure with a standard high sensitivity ohm meter by connecting at either end of the strip. The polarization resistance $R_p$ is determined from the relationship:

$$R_p = \left[\frac{B_a B_c MW}{2.3(B_a + B_c) \cdot \text{Density} \cdot 2F \cdot L^2 \rho}\right] \Delta t \left(\frac{R_1 R_2}{R_2 - R_1}\right) \quad \text{(Eq. 1)}$$

where:
 $B_a$ and $B_c$ are Tafel slopes of the anodic and cathodic reactions, respectively either determined separately or known values utilized,
 MW is the molecular weight of the metal of the test electrode, Density being its density,
 $\rho$ is the specific conductance of the metal,
 F is Faraday's constant,
 $L^2$ is the square of the length of the test electrode, and
 $R_1$ and $R_2$ are the resistance measurements over time period $\Delta t$.

The potential of the metal strip V is measured relative to the reference electrode. Performing these two measurements, that is, measuring the resistance across the length of the test electrode over a period of time $\Delta t$ and measuring the potential of metal strip V, may be performed independently at a frequency chosen by the operator without need to cease either of the measurements. In LPR, one would have to stop measurements, but this is not necessary with the method herein. An advantage over previous methods such as LPR is that continuous measurements of potential and resistance may be taken without interruption. This may be done by using a rolling or moving average or other suitable technique. Interruption and restarting measurements, as in prior methods, tends to be accompanied by inaccuracy immediately after the interruption, which is avoided in this method. Determining Rp in this way produces more meaningful values of current transients.

The localized corrosion may be calculated from Rp using equation 2. When a potential is applied to an electrode that is different from the rest potential then the electrode attempts to restore the balance through current flow. If only activation control is involved (i.e. no concentration or diffusion effects) then the slope of the line of the plot of I vs. E is Rp. Hence, from a change in E such as a pitting event and a knowledge of Rp, then the associated current of the event can be calculated by I=E/Rp:

$$I = \frac{\Delta V}{R_p} \quad \text{(Eq. 2)}$$

where: $\Delta V$ is a potential transient. This corrosion current transient may then be integrated over the transient life-time and together with MW and Faraday's laws (relating the quantity of the charge to the mass/mols of material) to provide a mass loss from the metal strip. This may then be converted to an assumed shape of localized corrosion; for example a spheroid of depth/radius ratio equal to some chosen value (gained from experience of the particular corroding system or direct measurement of localized corrosion from samples of the system). Using this assumed geometry for the volume of metal lost a penetration depth may be obtained.

The method determines localized corrosion rate by assuming that the Rp value obtained indirectly from the electrical resistance method (via calculation) can be attributed to the major corrosion event (localized corrosion) on the metal surface. This event is only monitored through potential (voltage) measurement. The further calculation to obtain I from Equation 2 utilizes the $\Delta V$ and the most recently calculated Rp (from most recent electrical resistance measurement). This value of I is then used to determine the mass loss from the metal strip due to the event. The mass lost is calculated from Faraday's laws that relate current (electrical charge) to mass. Then, knowing the mass related to the event and assuming a certain geometry of localized attack on the metal strip, a volume loss and depth of penetration may be calculated. Thus, the order in which voltage or electrical resistance is measured is not important. What is important is that the majority of the monitoring period is taken up by voltage data (potential measurement) as this is what captures the transient events. Electrical resistance measurements are only taken to ensure that Rp values are not changing too much and are relevant to the condition of the metal surface at the time transients are occurring.

In another non-limiting embodiment there is provided an apparatus for measuring localized corrosion that includes a test electrode having length L of a metal under investigation adapted to be in proximity to a conductive fluid. The apparatus further includes a temperature sensor (e.g. thermocouple or resistance thermometer) in proximity to the test electrode, and additionally includes a device (e.g. a potentiostat or galvanostat) for applying a potential to the test electrode as well as a device for measuring the resistance across the length of the test electrode, over a time period $\Delta t$ to give first and second resistance values $R_1$ and $R_2$. The apparatus further includes a device for measuring changes in conductance (e.g. a conductivity meter) due to temperature so that they may be subtracted or otherwise computationally removed from measurements of $R_1$ and $R_2$. There is also included in the apparatus a device (e.g. a computer) for determining polarization resistance Rp from Equation 1 given above. It should be realized that the conductance is not solution related but is related to the metal strip only and is the change in conductance with temperature (reciprocal of resistance). A goal here is to remove the effect of temperature swings on the measurement of resistance. In conventional ER (electrical resistance) probes an identical strip of metal is used (unexposed to the corroding environment) that is connected so as to nullify any temperature effect on the measurement of resistance on the exposed metal strip. As this corrosion monitoring technique requires a computer for the general calculations, it has been found that the probe may be simplified by not including the second identical strip and replacing it with a thermocouple to accurately measure the temperature and thus mathematically compensate for temperature swings through calculation of the change in resistance due to temperature alone (hence the need for the specific resistance of the metal under test). The apparatus may include a reference electrode.

The method and apparatus of the present invention may be implemented as a set computer executable of instructions on a computer readable medium, including, but not necessarily limited to, ROM, RAM, CD-ROM, Flash RAM or any other computer readable medium, now known or unknown that when executed cause a computer to implement the functions of the present invention.

Examples of the more important features thus have been summarized rather broadly in order that the detailed description thereof that follows may be better understood, and in order that the contributions to the art may be appreciated. There are, of course, additional features of the invention that will be described hereinafter and which will form the subject of the claims appended hereto.

BRIEF DESCRIPTION OF THE DRAWINGS

For detailed understanding, reference may made to the detailed description of various disclosed embodiments, taken in conjunction with the accompanying drawings, in which like elements have been given like numerals, wherein:

FIG. 1A is a schematic illustration of a strip of a metal of interest in its original state, whereas

DETAILED DESCRIPTION OF EXEMPLARY EMBODIMENTS

Figure 1A:
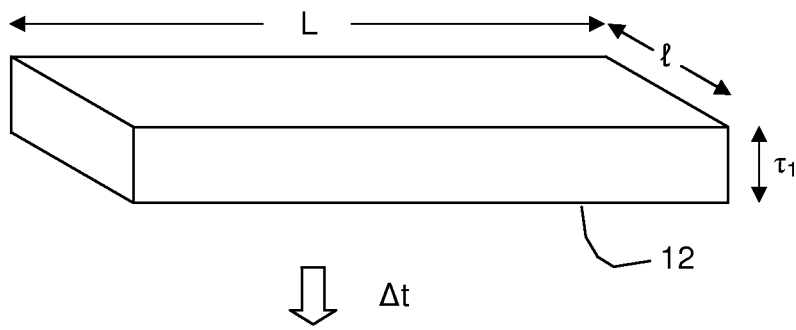

Methods and apparatus for the detection and characterization of the corrosion behavior in systems where localized corrosion occurs (in one non-limiting embodiment, in the form of pitting) and is quantitatively evaluated are described. The severity, frequency and time/space distribution of the localized events may be determined from potential and current measurements recorded from the corroding systems.

More specifically, in one non-limiting embodiment, localized corrosion has been determined semi-quantitatively previously by measuring the galvanic current between two electrodes and monitoring the potential of the couple using a third reference electrode. This is typically known as current/voltage (electrochemical) noise (ECN). The technique correlates the two signals using a range of mathematical methods to calculate the general corrosion rate ($R_p = \Delta V/\Delta I$) and estimate the likelihood of localized corrosion ($LI = \sigma_i/i_{rms}$), where LI refers to Localization Index, a refers to the change in current, and $i_{rms}$ refers to the root mean square of the current. The current analysis of localized corrosion based on ECN provides indications of the likelihood of localized corrosion (LI) without specific reference to the surface affected, or the number and distribution of those localized events. LI relates to the degree of localized corrosion compared to general corrosion, i.e., the greater the LI the higher the probability of localized corrosion. However, the polarization caused by coupling the two galvanically coupled electrodes takes away a measure of sensitivity in the technique as the two galvanically coupled electrodes are not at their individual rest potentials. This polarization can make it less apparent to identify individual localized events. Localized events can occur on any one of the two electrodes which in some way contributes to the noise element of the data and a measure of inaccuracy when it comes to analysis.

Another method that gives an indication of localized corrosion is by monitoring the potential of a single test electrode with respect to a reference electrode, known as potential noise. This method can detect potential excursions caused by localized events, however, without any current information it is not realistically possible in real time to correlate the significance or magnitude of a potential transient in terms of metal loss.

The Localized Corrosion Monitoring (LCM) technique herein was developed by switching between periods of potential monitoring and potentiostatic control at the rest potential. During the potentiostatic measurement the polarization of the test electrode is minimized and both current and potential data are obtained. It is possible to identify individual localized events (i.e. transients) through the reconstruction of current transients. This enables a quantitative measure of the amount of current involved in each event to be obtained, leading to possibilities of measuring the rate of localized corrosion associated with each transient (i.e. pit growth). The LCM technique depends on the analysis of data due to the regular switching between free potential measurement and polarization at the rest potential. Such signals can lead to current transient truncation and thus a possible underestimation of the total charge in each pitting event, i.e. pit depth estimation.

The present methods and apparatus provide for continuous localized corrosion monitoring and real time analysis of the monitored data. Real-time system monitoring of the corrosion status of operating equipment is enabled. In laboratory investigations, the apparatus herein is expected to provide information on localized corrosion behavior that may be directly correlated with corrosion attacks.

This apparatus and method herein provide continuous monitoring of the sudden changes in the corrosion potential with time and can provide information about localized corrosion rate and processes. These changes develop dynamically in the form of transient responses in potential transient measurements. While numerous methods have been used to measure general corrosion (e.g. linear polarization resistance (LPR), electrical resistance, EIS, electrochemical noise (ECN)), there have been few analysis methods for characterizing localized corrosion.

U.S. Pat. No. 6,280,603 to Jovancicevic discloses a potentiostatic electrochemical noise (P-ECN) invention and provides quantitative measure of localized corrosion in terms of type, frequency, distribution and penetration rate (this patent is hereby fully incorporated herein by reference). Three different types of single current/potential transients may be identified: (i) initiation/propagation (Type I), (ii) initiation/partial repassivation (Type II), and (iii) initiation/repassivation (Type III), and one multiple initiation/propagation (Type IV) transients are recorded over time (FIG. 1 in U.S. Pat. No. 6,280,603). The transients may be defined as a sudden cathodic shift in potential or anodic shift in current at open-circuit or constant potential, respectively. For a given system of objects to be monitored, depending on the metal or material examined, a transient may be a potential shift of 0.5 mv/sec or an anodic shift of $>0.1$ $\mu A/cm^2/sec$. For some typical systems, the Type I and II transients may be chosen as transients that last, for example, 5 seconds, while Type III transients may be chosen as those that last between 30 seconds and 200 seconds, and Type IV as those that last 200 seconds; these are non-limiting examples. The relative differences of the amplitudes and frequencies of various transients may be indicative of the types of corrosive attacks present in any active system. These electrochemical noise data can provide an indication of the type of corrosion damage occurring; and may be used to indicate the nature of localized attack. The severity of localized corrosion may be measured by the penetration rate of individual pits.

Based on the magnitude, duration and relative rate of decrease and/or increase of potential and current signals, four different types of transients can be observed in the LCM time records and classified as: Type I initiation/propagation (IP), Type II initiation/partial repassivation (IPR), Type III initiation/repassivation (IR) and Type IV initiation/repassivation/propagation (IRP) transients. Type III is of less concern because the site of the corrosion undergoes repassivation. Type IV transients are indicative of multiple pits occurring that are generally large in number, more or less active, uniformly distributed, smaller and shallower than the IP (Type I) and IPR (Type II). This transient analysis of the potential/current time dependence will be used in quantifying localized corrosion activity on the carbon steel and stainless steel tests.

The occurrence and amplitude of current/potential transients with time are directly related to the number, magnitude (depth) and distribution of localized corrosion events (e.g. pits). Thus, as the transients are longer, and as the amplitudes of the transients are larger, the larger the area affected by corrosion. Also when an area affected by corrosion is larger, the depth of the corrosion is less.

By correlating data acquired from monitored systems with the above parameters, information on the severity and the feature of corrosion damage on the monitored objects can be obtained. Similarly, the effectiveness of corrosion control measures, such as chemical inhibition, or the need for such measures, can be determined.

Both potential and current LCM data may be acquired by alternatively recording with time using for example 30 seconds on (current) and 30 seconds off (potential) potentiostatic control/open circuit potential sequence. However, in one embodiment, it is helpful if the entire transient on the current and potential sides are measured to determine pitting parameters so that charge, mass and volume displaced from localized corrosion pits may be estimated. (Potential transients can be converted into equivalent current transients, e.g. by using $R_p=\Delta V/\Delta I$, by which the charge can be estimated. An alternative approach to estimate the approximate charge of a potential transient is via the double layer capacitance and potential relationship.) Therefore, operator intervention and/or software may be used to both recognize the onset of current transients (or potential transients), and to begin or resume the alternate cycling after transients have substantially terminated. LCM relies on the measurements of time of occurrence, magnitude, duration, frequency and distribution of distinct potential (negative) and current (positive) transients as a result of initiation and/or propagation/repassivation of localized corrosion events (e.g. pitting, crevice).

Localized corrosion, as indicated by the previously described transient Types I-IV, means pitting has happened locally and the extent of the event, both area and depth of penetration, may be determined directly from the current and potential measurements.

The methods and apparatus described herein make it easy to convert discrete transients in the potential fluctuations into current data. Individual localized events may be monitored in their entirety and given a meaningful current magnitude. The number of coulombs of current passed by a single transient event may be calculated and related to the magnitude of localized events (e.g. pit depth).

As noted, the potential of a test electrode is monitored with respect to a reference electrode. Periodically, a polarization is applied to the test electrode around its rest potential and $R_p$, previously determined using LPR, EIS, LCM or ECN, that is related to a typical potential transient caused by a localized corrosion event occurring on the test electrode, recorded. However, the methods and apparatus herein use an electrical resistance (ER) technique to determine $R_p$. The ER technique has two parts which may be combined.

Resistance Calculation

Figure 1B:
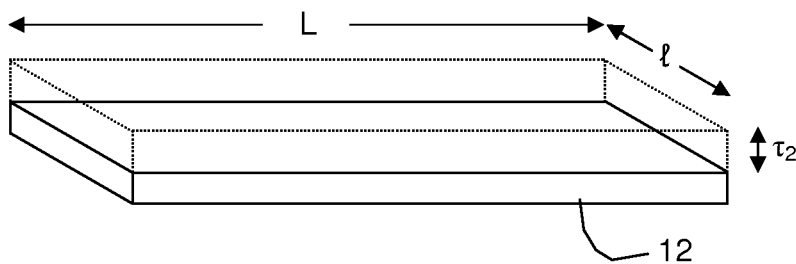
FIG. 1B is a schematic illustration of the metal strip of FIG. 1A after a time period $\Delta t$ where the thickness of the metal strip is reduced by an amount $\tau_2$.

Schematically shown in FIG. 1A is a test electrode 12 having a length L between two opposite or opposing ends, a width l and an original thickness $\tau_1$. After passage of time $\Delta t$, the thickness of test electrode 12 is reduced by amount $\tau_2$ as shown in FIG. 1B. Keeping in mind V=IR, where V is potential difference, I is current and R is resistance, the resistance at the two different times may be expressed as follows:

$$R_1 = \rho \frac{L}{\ell \tau_1} \quad \text{(Eq. 3)}$$

$$R_2 = \rho \frac{L}{\ell \tau_2} \quad \text{(Eq. 4)}$$

where $\rho$ is the specific conductance of the metal, $R_2 > R_1$ and $\tau_2 < \tau_1$.

Rearranging gives:

$$\tau_2 = \frac{\rho L}{\ell} \cdot \frac{1}{R_2} \quad \text{(Eq. 5)}$$

$$\tau_1 = \frac{\rho L}{\ell} \cdot \frac{1}{R_1} \quad \text{(Eq. 6)}$$

Taking the difference gives:

$$\tau_1 - \tau_2 = \frac{\rho L}{\ell}\left[\frac{1}{R_1} - \frac{1}{R_2}\right] \text{ over } \Delta t \text{ time} \quad \text{(Eq. 7)}$$

Therefore, corrosion rate (CR) (length/time):

$$CR(L/t) = \frac{\tau_1 - \tau_2}{t_2 - t_1} = \frac{\rho L}{\ell}\left[\frac{1}{R} - \frac{1}{R_2}\right] \Big/ (t_2 - t_1) \quad \text{(Eq. 8)}$$

$$CR(L/t) = \frac{\rho L}{\ell} \cdot \left[\frac{R_2 - R_1}{R_1 \cdot R_2}\right] \Big/ (t_2 - t_1) \quad \text{(Eq. 9)}$$

The times $t_1$ and $t_2$ may be as close as possible and still give an accurate corrosion rate. It is a general corrosion rate averaged over the entire metal strip 12 (test electrode).

Electrochemistry Calculation

The Stearn-Geary equation may be expressed as Equation 10 for unit area i.e. coulombs$^{-1}$cm$^{-2}$ where $B_a$ and $B_c$ are Tafel slopes of the anodic and cathodic reactions, respectively, $I_c$ is the general corrosion rate (CR in Equations 9 and 10). Ba and Bc may be measured from an electrochemical potentiodynamic sweep of a specimen in the environment under investigation. They are taken as the slope of the V/I curves close to the rest potential. In known environments they are well characterised for carbon steel and can therefore also be taken from literature. The value 2.3 in Equation 10 is a constant arising from conversion from natural logs to base 10 logs.

$$\frac{\Delta E}{\Delta I} = \frac{B_a \cdot B_c}{2.3 \cdot I_c (B_a + B_c)} = R_p \qquad \text{(Eq. 10)}$$

Solving for $I_c$ gives Equation 11.

$$I_c = \frac{B_a \cdot B_c}{(B_a + B_c)2.3} \cdot \frac{1}{R_p} \qquad \text{(Eq. 11)}$$

Combining Resistance and Electrochemistry Calculations

To obtain $I_c$ from ER measurements, it is needed to convert penetration rate to a current using Faraday's Law, i.e. mpy→$I_c$. In the non-limiting instance of carbon steel, the Density is 7.8 g/cm$^3$. Area=L·l, and thus volume change is L·l($\tau_1-\tau_2$). Since Density=Mass/Volume, therefore:

$$\text{Mass} = 7.8 \cdot L \cdot \ell \cdot (\tau_1 - \tau_2) \qquad \text{(Eq. 12)}$$

$$\text{Mass} = \frac{I_c \cdot MW \cdot \Delta t}{2F} \qquad \text{(Eq. 13)}$$

where MW is the molecular weight of the strip 12 metal and F is Faraday's constant. Making the substitution for mass gives:

$$\frac{I_c \cdot MW \cdot \Delta t}{2F} = 7.8 \cdot L \cdot \ell \cdot (\tau_1 - \tau_2) \qquad \text{(Eq. 14)}$$

$$I_c = \frac{7.8 \cdot L \cdot \ell \cdot (\tau_1 - \tau_2) \cdot 2F}{MW \cdot \Delta t} \qquad \text{(Eq. 15)}$$

It will be understood that consistency of units will require conversion factors for units such as converting centimeters to inches, etc., which are not included. Replacing $\tau$ with the resistances (see Resistance Calculation) gives:

$$I_c = \frac{7.8 \cdot L \cdot \ell \cdot 2F}{MW \cdot \Delta t} \cdot \frac{\rho L}{\ell} \left[\frac{1}{R_1} - \frac{1}{R_2}\right] \qquad \text{(Eq. 16)}$$

$$I_c = \frac{7.8 \cdot 2F \cdot L^2 \cdot \rho}{MW} \cdot \frac{1}{\Delta t} \cdot \left[\frac{1}{R_1} - \frac{1}{R_2}\right] \qquad \text{(Eq. 17)}$$

Recalling Equation 11 and making the substitution for $I_c$ gives:

$$\frac{1}{R_p} \cdot \frac{B_a \cdot B_c}{2.3(B_a + B_c)} = \frac{7.8 \cdot 2F \cdot L^2 \cdot \rho}{MW} \cdot \frac{1}{\Delta t} \cdot \left[\frac{1}{R_1} - \frac{1}{R_2}\right] \qquad \text{(Eq. 17)}$$

Solving for $R_p$ gives:

$$R_p = \frac{B_a \cdot B_c \cdot MW \cdot \Delta t}{2.3(B_a + B_c) \cdot 7.8 \cdot 2F \cdot L^2 \cdot \rho \cdot \left[\frac{1}{R_1} - \frac{1}{R_2}\right]} \qquad \text{(Eq. 18)}$$

$$R_p = \left[\frac{B_a \cdot B_c \cdot MW}{2.3(B_a + B_c) \cdot 7.8 \cdot 2F \cdot L^2 \cdot \rho}\right] \Delta t \Big/ \left[\frac{R_2 - R_1}{R_1 R_2}\right] \qquad \text{(Eq. 19)}$$

$$R_p = \left[\frac{B_a \cdot B_c \cdot MW}{2.3(B_a + B_c) \cdot 7.8 \cdot 2F \cdot L^2 \cdot \rho}\right] \Delta t \left(\frac{R_1 R_2}{R_2 - R_1}\right) \qquad \text{(Eq. 20)}$$

Where the Equation 17 may be stated generally at Equation 19:

$$R_p = \left[\frac{B_a B_c MW}{2.3(B_a + B_c) \cdot \text{Density} \cdot 2F \cdot L^2 \rho}\right] \Delta t \left(\frac{R_1 R_2}{R_2 - R_1}\right) \qquad \text{(Eq. 1)}$$

$R_p$ may thus now be used as in the LCM technique, such as that described in US Patent Application Publication 2006/0144719 A1, incorporated herein in its entirety by reference, i.e. converting potential transients to current and integrating to obtain resistance change and hence metal lost due to pitting events.

Figure 2:
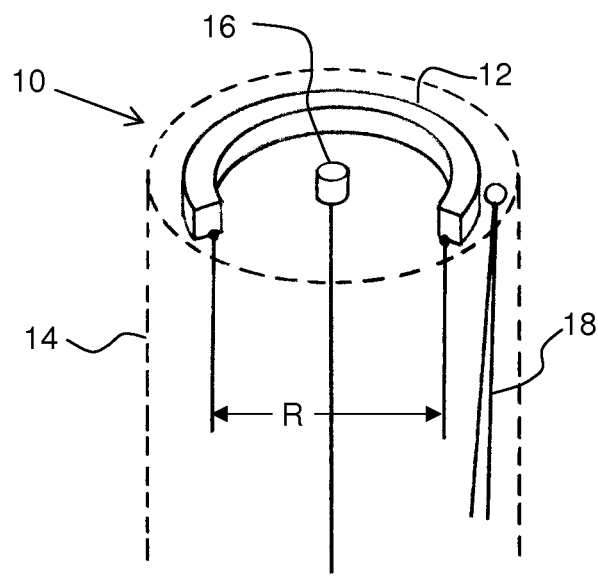
FIG. 2 is a schematic illustration of one non-limiting embodiment of an apparatus probe herein illustrating a metal strip, a reference electrode and a thermocouple in close proximity.

Referring to FIG. 2, shown is a probe 10 having a test electrode or metal strip 12 of a metal under investigation that undergoes resistance changes due to corrosion. The wires from either end of metal strip 12 are used for connection to instrumentation for both continuous potential monitoring and resistance measurement. The measurements may be completely independent of each other and the frequency of measurements of either may be selected over any time period. The test electrode 12 is exposed at or beyond the surface of probe 10 to a corrosive environment. In one non-limiting embodiment, the test electrode is flush mounted in probe body 14, which may be a polymer or other insulating material. In the particular embodiment shown in FIG. 2, test electrode or metal strip 12 is curved to save space, but could be rectilinear as seen in FIGS. 1A and 1B. It still has a length L. Probe 10 also contains a reference electrode 16 which is exposed to the corrosive environment at or beyond the surface of the probe; and in one non-limiting embodiment may also be flush mounted to the surface of probe body 14. The reference electrode 16 may alternatively be simply part of the probe body itself, provided it does not connect to another metallic or conductive component. Measurements of resistance are made at the ends of test electrode 12 as shown in FIG. 2. Metal strip 12 in another non-restrictive embodiment may be simply a wire loop extending into the fluid, with only the ends extending into the probe body 14 (polymer, other insulative material, e.g.) for connection to the electrical leads.

The method and apparatus additionally includes a temperature sensor 18, in one non-restrictive version a thermocouple, for sampling the temperature of the metal 12. Conventional ER probes use an identical metal sample, insulated from the environment, to compensate for resistance change caused by temperature. The method and apparatus herein instead employs the recorded temperature (e.g. from thermocouple 18) and software calculations to produce a calculated compensation to the measured resistance. From the known specific resistance of the sample material, which may be obtained from physical tables or measured at the time of probe manufacture, the resistance due to temperature is subtracted from the measured resistance at 12. The resultant resistance is used to determine Rp.

The method and apparatus described herein are particularly appropriate to use where there is a limited amount of a conductive or corrosive fluid. For instance, the probe described above is effective in measuring localized corrosion for aqueous films of physical thicknesses of about 10 microns or less; in an alternative embodiment for transient aqueous films of thicknesses of about 10 microns or less. However, it should be understood that the film thickness may range from the thinnest that is able to conduct an electrical charge to an infinite thickness. The fact that the apparatus and method may be practiced to detect transient conditions demonstrates that the technique does not require continuous wetting of the surface and will record data only during wetted periods (since the surfaced will not be corroding when not wetted). That is, the requirement for data collection is a conductive film between the reference and the specimen (metal 12). This makes the apparatus less sensitive to occasional hydrocarbon wetting compared to the conventional LCM technique which requires the reference and auxiliary electrodes to be simultaneously wetted to perform an LPR scan. Here, the ER measurement does the evaluation whether wetted or not. However, in both types of techniques, the reference electrode to sample electrode need to be wet with water during potential readings. This permits the LCM technique to be more broadly applicable, particularly where only small amounts of corrosive fluid are available or desired (such as for safety reasons). The apparatus and methods herein are thus also more useful in environments were only condensing water vapor is available as the conductive/corrosive medium. Further, by a "limited conductivity fluid" is meant one that has an electrical conductivity of about $10^{-4}$ Siemens/m or less. Non-limiting examples of limited conductivity fluids include, but are not necessarily limited to water, particularly sea water, drinking water, condensate in boilers and pipelines, formation water from oil and gas production, any water commonly occurring in industrial processes.

Other considerations and features of the methods and apparatus described herein include, but are not necessarily limited to the following.

The reference electrode may be resistant to localized corrosion and hold a steady potential. This is a requirement if one wishes to incorporate the probe into a single probe the conventional LCM technique and the present inventive resistance technique. This combination may be worth doing as then general corrosion rates may be obtained in addition to localized measurements, rather than from two separate techniques and apparatus. Again, no polarization is required in the present method and apparatus—polarization is required only if the two techniques are combined.

The ER technique should be utilized in a similar way to the polarization technique to obtain representative Rp's over the period of potential monitoring. The application of the electrical resistance measurement needs be only a small percentage of the total test time. One guideline is to measure the resistance every hour and utilize a rolling average (or other suitable technique) for interpreting the potential data. Electrical resistance is less sensitive than LPR to small changes in corrosion rate over short periods of time. It may be worth noting that there are several commercial ER instruments that have increased sensitivity built into their circuitry so that they are close to LPR.

The methods and apparatus described herein allow for determinations of changes in the rate of propagation of the depth of pits with time, or penetration rate, from the measured transients of any one of Types I-IV. Using this information the approximate mass or volume of metal corroded due to localized corrosion may be determined. The present method and apparatus therefore allow for accurate determination of localized corrosion. The number of pits that occur and their depth of penetration may be determined from this technique once the Rp has been obtained from the ER measurements. The assumption that all or almost all of the corrosion is localized corrosion is strengthened by the fact that the types of corrosion described herein above, especially the "active" Type I and II transients, directly indicate ongoing localized corrosion. Without the transients that indicate localized corrosion there would be no analysis of corrosion penetration rates.

The present methods and apparatus provide for features including, but not necessarily limited to, an internal potentiostat, an ohmmeter, a conductivity meter, a zero resistance ammeter and internal PC (personal computer) or other computing apparatus for monitoring, measuring and analyzing data. The PC may include any operating system and run software for data analysis that accomplishes the purposes and goals described herein.

In another embodiment, the methods and apparatus are implemented as a set of computer-executable of instructions on a computer readable medium, comprising ROM, RAM, CD-ROM, Flash RAM or any other computer readable medium, now known or unknown that when executed cause a computer to implement the functions of the present invention.

In order to determine the corrosion rate, the test electrode may be fabricated from the same or reasonably similar material as the item of concern (i.e. the component, article), in the case of using the methods and/or apparatus to devise a technique, algorithm or program to protect an item or items of concern. Generally, the material is a metal or metal alloy. Although the auxiliary electrode, if used, may be formed of any material, including the same material as the test electrode, the auxiliary electrode may be comprised of material which is inert in the particular environment of interest. For example, the auxiliary electrode may be of a material including, but not necessarily limited to, platinum, nickel-based (e.g., HASTELLOY® C276 alloy), iron based (e.g., stainless steel) or a chromium-based alloy, or mixtures and alloys thereof, or any other electrically conductive, non-corrosive material. Similar to the auxiliary electrode, the reference electrode can comprise any suitable material that is known to the industry, but most conveniently can comprise an inert, electrically conductive material.

In operation, the test, optional auxiliary, and reference electrodes are disposed in the same or very similar environment as the component of interest is or will be, in a spaced relation to one another, but in proximity. Proximity is defined herein as 1 cm or less apart. The proximity should be close enough to be affected by the same corrosive environment as all elements of the probe. A very close proximity (1 mm) has the advantage that only a short or thin conductive film is required for potential measurement; but has the disadvantage that it may easily be bridged by conductive fouling, such as iron sulfide.

While various embodiments and alternatives have been shown and described, various modifications and substitutions may be made thereto without departing from the spirit and scope of the invention, which are defined only by the appended claims. Accordingly, it is to be understood that the present invention has been described by way of illustrations and not limitation. For instance, alternative devices and machines may be employed to collect and analyze the data other than those specifically mentioned.

The present invention may suitably comprise, consist or consist essentially of the elements disclosed and may be practiced in the absence of an element not disclosed.

The words "comprising" and "comprises" as used throughout the claims is to interpreted "including but not limited to".

What is claimed is:

1. An apparatus for measuring localized corrosion comprising:
   (a) a single test electrode having length L of a metal under investigation, adapted to contact a conductive fluid, and a reference electrode;
   (b) a temperature sensor in proximity to the single test electrode;
   (c) an ohmmeter configured for measuring the resistance across the length L of the single test electrode over a time period $\Delta t$ to give first and second resistance values $R_1$ and $R_2$;
   (d) a device configured for calculating corrosion rates from changes in resistance due to corrosion and subtracting them from measurements of $R_1$ and $R_2$;
   (e) a device configured for measuring potential difference between the reference electrode and the single test electrode;
   (f) a computer programmed for determining polarization resistance $R_p$ from the relationship:

$$R_p = \left[\frac{B_a B_c MW}{2.3(B_a + B_c) \cdot \text{Density} \cdot 2F \cdot L^2 \rho}\right] \Delta t \left(\frac{R_1 R_2}{R_2 - R_1}\right) \quad \text{(Eq. 1)}$$

where:
   $B_a$ and $B_c$ are Tafel slopes of anodic and cathodic reactions, respectively, obtained separately or from known values,
   MW is the molecular weight of the metal of the single test electrode, Density being its density,
   $\rho$ is the specific conductance of the metal,
   F is Faraday's constant,
   $L^2$ is the square of the length of the single test electrode, and
   $R_1$ and $R_2$ are the resistance measurements over time period $\Delta t$; and; and
   (g) the computer programmed for calculating the localized corrosion from V=Rp·I, which device may be the same as or different from the devices in d) and e), where I is current, and where the current is calculated by an electrical resistance (ER) technique.

2. The apparatus of claim 1 where the temperature sensor is selected from the group consisting of a thermocouple, resistance thermometer, and combinations thereof.

3. The apparatus of claim 1 where the single test electrode and the reference electrode are flush mounted on a probe.

4. The apparatus of claim 1 configured where the localized corrosion measured is selected from the group of characteristics consisting of: i) the number of corrosion events, ii) the duration of corrosion events, iii) surface area of a corrosion event, iv) depth of penetration of a corrosion event, v) rate of penetration of a pit associated with a corrosion event, vi) volume of metal displaced by corrosion event and vii) the type of localized corrosion event.

5. The apparatus of claim 1 configured where the localized corrosion measured is a rate of penetration of a pit associated with the localized corrosion event estimated from a measured rate of change of the open circuit (free) potential and a measured resistance of the sample.

6. The apparatus of claim 1 further comprising a potentiostat or a galvanostat, and a conductivity meter and where the device for calculating corrosion rates from changes in resistance is the computer.

7. An apparatus for measuring localized corrosion comprising:
   (a) a single test electrode having length L of a metal under investigation, adapted to contact a conductive fluid, and a reference electrode;
   (b) a temperature sensor in proximity to the single test electrode, where the temperature sensor is selected from the group consisting of a thermocouple, resistance thermometer, and combinations thereof;
   (c) an ohmmeter configured for measuring the resistance across the length L of the single test electrode over a time period $\Delta t$ to give first and second resistance values $R_1$ and $R_2$;
   (d) a device configured for calculating corrosion rates from changes in resistance due to corrosion and subtracting them from measurements of $R_1$ and $R_2$;
   (e) a device configured for measuring potential difference between the reference electrode and the single test electrode;
   (f) a computer programmed for determining polarization resistance $R_p$ from the relationship:

$$R_p = \left[\frac{B_a B_c MW}{2.3(B_a + B_c) \cdot \text{Density} \cdot 2F \cdot L^2 \rho}\right] \Delta t \left(\frac{R_1 R_2}{R_2 - R_1}\right) \quad \text{(Eq. 1)}$$

where:
   $B_a$ and $B_c$ are Tafel slopes of the anodic and cathodic reactions, respectively, obtained separately or from known values,
   MW is the molecular weight of the metal of the single test electrode, Density being its density,
   $\rho$ is the specific conductance of the metal,
   F is Faraday's constant,
   $L^2$ is the square of the length of the single test electrode, and
   $R_1$ and $R_2$ are the resistance measurements over time period $\Delta t$; and
   (g) the computer programmed for calculating the localized corrosion from V=Rp·I, which device may be the same as or different from the devices in d) and e), where I is current, where the current is calculated by an electrical resistance (ER) technique, and where the localized corrosion measured is selected from the group of characteristics consisting of: i) the number of corrosion events, ii) the duration of corrosion events, iii) surface area of a corrosion event, iv) depth of penetration of a corrosion event, v) rate of penetration of a pit associated with a corrosion event, vi) volume of metal displaced by corrosion event and vii) the type of localized corrosion event.

8. The apparatus of claim 7 where the single test electrode and the reference electrode are flush mounted on a probe.

9. The apparatus of claim 7 configured where the localized corrosion measured is a rate of penetration of a pit associated with the localized corrosion event estimated from a measured rate of change of the open circuit (free) potential and a measured resistance of the sample.

10. The apparatus of claim 7 further comprising a potentiostat or a galvanostat, and a conductivity meter and where the device for calculating corrosion rates from changes in resistance is the computer.

11. The apparatus of claim 1 where the conductive fluid is a limited conductivity fluid having an electrical conductivity of about 10-4 Siemens/m or less.

12. The apparatus of claim 7 where the conductive fluid is a limited conductivity fluid having an electrical conductivity of about 10-4 Siemens/m or less.

13. An apparatus for measuring localized corrosion comprising:
   (a) a single test electrode having length L of a metal under investigation, adapted to contact a conductive fluid having an electrical conductivity of about 10-4 Siemens/m or less, and a reference electrode;
   (b) a temperature sensor in proximity to the single test electrode;
   (c) a conductivity meter configured to measure changes in conductance;
   (c) an ohmmeter configured for measuring the resistance across the length L of the single test electrode over a time period $\Delta t$ to give first and second resistance values $R_1$ and $R_2$;
   (d) a computer programmed for calculating corrosion rates from changes in resistance due to corrosion and subtracting them from measurements of $R_1$ and $R_2$;
   (e) a device selected from the group consisting of a potentiostat and a galvanostat configured for measuring potential difference between the reference electrode and the single test electrode;
   (f) the computer programmed for determining polarization resistance Rp from the relationship:

$$R_p = \left[\frac{B_a B_c MW}{2.3(B_a + B_c) \cdot \text{Density} \cdot 2F \cdot L^2 \rho}\right] \Delta t \left(\frac{R_1 R_2}{R_2 - R_1}\right) \quad \text{(Eq. 1)}$$

where:
   $B_a$ and $B_c$ are Tafel slopes of anodic and cathodic reactions, respectively, obtained separately or from known values,
   MW is the molecular weight of the metal of the single test electrode, Density being its density,
   $\rho$ is the specific conductance of the metal,
   F is Faraday's constant,
   $L^2$ is the square of the length of the single test electrode, and
   $R_1$ and $R_2$ are the resistance measurements over time period $\Delta t$; and
   (g) the computer programmed for calculating the localized corrosion from V=Rp·I, which device may be the same as or different from the devices in d) and e), where I is current, and where the current is calculated by an electrical resistance (ER) technique.

* * * * *